United States Patent
Nickel

(10) Patent No.: US 8,530,502 B2
(45) Date of Patent: *Sep. 10, 2013

(54) APPLICATION METHODS TO RAPIDLY ALTER DISEASE AND INJURY STATES USING MOLECULAR TRANSPORT OF B6

(75) Inventor: Alfred A. Nickel, Camino, CA (US)

(73) Assignee: Dr. N's Health Care Products, LLC, Zephyr Cove, NV (US)

( * ) Notice: Subject to any disclaimer, the term of this patent is extended or adjusted under 35 U.S.C. 154(b) by 488 days.

This patent is subject to a terminal disclaimer.

(21) Appl. No.: 12/437,816

(22) Filed: May 8, 2009

(65) Prior Publication Data

US 2009/0238809 A1    Sep. 24, 2009

Related U.S. Application Data

(63) Continuation of application No. 11/324,693, filed on Dec. 30, 2005, now Pat. No. 7,550,488.

(51) Int. Cl.
*A61K 31/44* (2006.01)
*A61K 31/675* (2006.01)
*A61K 31/195* (2006.01)
*A61K 31/16* (2006.01)
*A01N 57/00* (2006.01)
*A01N 37/44* (2006.01)

(52) U.S. Cl.
USPC ............ 514/345; 514/78; 514/89; 514/351; 514/563; 514/569; 514/629; 514/818; 514/905; 514/936

(58) Field of Classification Search
USPC ................................. 514/345, 563
See application file for complete search history.

(56) References Cited

U.S. PATENT DOCUMENTS

| | | |
|---|---|---|
| 5,776,859 A | 7/1998 | Nickel |
| 5,780,242 A | 7/1998 | Nickel |
| 7,550,488 B2 * | 6/2009 | Nickel ......................... 514/345 |
| 2004/0116470 A1 | 6/2004 | Nickel |

FOREIGN PATENT DOCUMENTS

WO    2005/060964    7/2005

OTHER PUBLICATIONS

Irnich D, et al., "ATP affects both axon and Schwann cells of unmyelinated C Fibers"., Pain 92:343-350 (2001).
Bernstein, Allan L.,, "Vitamin B6 in clinical neurology.". Annals N.Y. Academy Science, 585:250-260 (1990).
Author: Grandpa's Compounding Pharmacy, "New Medicine Heals 6 Times Faster", published in The Clipper on Apr. 26, 2005 at p. 10 (El Dorado County, California).
Author: Grandpa's Compounding Pharmacy, "Man Uses Special Vitamin Cream on Temples and Can Now See out of Blind Eye", published in The Clipper on Aug. 16, 2005 at p. 22 (El Dorado County, California).

* cited by examiner

*Primary Examiner* — John Pak
*Assistant Examiner* — Nathan W Schlientz
(74) *Attorney, Agent, or Firm* — Temmerman Law Office; Mathew J. Temmerman

(57) ABSTRACT

The present invention discloses methods of application employing B51B6 vitamins in molecular transport creams or gels to deliver B6 in a high dose to bring about therapeutic ways in human or mammal tissues to reverse a disease process or injury to bring about normal function of the affected tissues. Examples of disease changes to normal include, but are not limited to strokes, cellulitis, facial acne, precancerous lesions, nerve injury like paresthesia, periorbital hematoma, pentathol general anesthesia recovery, headaches, improved sight, hypothyroidism, dental pain, dental gingivitis, insect bites, delayed hypersensitivity states, phlebitis of veins and synergism of steroid activity.

9 Claims, No Drawings

APPLICATION METHODS TO RAPIDLY ALTER DISEASE AND INJURY STATES USING MOLECULAR TRANSPORT OF B6

RELATED APPLICATIONS

This application is related to and is a continuation of non-provisional patent application Ser. No. 11/324,693, filed Dec. 30, 2005 now U.S. Pat. No. 7,550,488 and for which a Notice of Allowance has issued.

BACKGROUND

Background of the Invention

Molecular Transport of vitamin B6 was described to occur in outpatient oral surgical procedures in U.S. application Ser. No. 10/318,940. Continued clinically usage of B6, either as an analog or pure pyridoxine form incorporated in either a molecule transport system like meperidine or a molecular/molecule system like a cream or gel in which the cream or gel behaves identical to a carrier system. Vitamin B6 was added to mixture or gel or cream to permit a synergistic enhancement of B6 activity on a cellular level. Details of B5/B6 cream or gel are disclosed in U.S. patent application Ser. No. 12/074,893 and WIPO.

SUMMARY OF THE INVENTION

Vitamin B6, either in pyridoxine or analog form, was used to clinically reverse disease and injury states in humans by influencing theoretical biochemical known pathways that for one reason or another cannot function normally or a injury event, like a arterial bleed in the brain, that can be manipulated by B6 action to reverse a tissue damaging event through altered metabolic rates. Thus by topical application of a rapid wound healing B51B6 mixture overlying an organ or injury site, the clinical abnormally can be reversed to a normal state in the living organism.

BRIEF DESCRIPTION OF THE FIGURES

The foregoing aspects and many of the attendant advantages of the invention will become more readily appreciated as the same becomes better understood by reference to the following detailed description, when taken in conjunction with the accompanying drawings, wherein:

DETAILED DESCRIPTION OF THE INVENTION

The following description is presented to enable a person of ordinary skill in the art to make and use various aspects and examples of the present invention. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described and shown, but is to be accorded the scope consistent with the appended claims.

Topical application of a transported B6 mixture can reverse facial acne either in conjunction with antibiotic therapy or without antibiotics. The clinical course is usually a facial acne or blemish in the age group of 16 years old to 36 years old. Application of the B6 mixture has in 8 adult cases resulted in normal skin without the blemishes present when other accepted methods of dermatological care have failed. Resolution of the acne problem occurs over a 2-week period of time. One case report of 72-year-old female with precancerous facial lesions documented through biopsy resulted in complete resolution of the precancerous lesions in 2 weeks for the first time in 15 years by applying a B6 mixture 3 to 4 times a day to the affected facial tissue. One useful observation in the cases was that the mixture could cake on the face. Addition of tap water to the cakey mixture renewed the penetration process by the ointment.

A more dramatic case report in using the B6 mixture concerns the rapid reversal of submandibular cellulitis in 47-old-male hospitalized for this life-threatening event. The clinical facial submandibular cellulitis in involving the submaxillary, sublingual and submental spaces from a dental infective origin becomes of serious concern for airway management when the patient presents with marked inability to open their mouth and the submandibular tissues become "board-like" to digital exam. Concern of a pending Ludwig's Angina cellulitis motivates both the patient and clinician to aggressive antibiotic, diagnostic and surgical/anesthesia management in a hospital setting.(6)

Using the B5 (5%.) B6 (30%) in a transmolecular cream, a stunning rapid reversal of such a clinical situation in a 47-year old male is described. This patient had been on oral antibiotics 48 hours for a lower left molar infection (#18) without any help and presented at noon as afebrile, unable to open his teeth more than 1 mm, with marked submandibular cellulitis infection requiring hospitalization for management in the prior 24 months. Prompt admission to a hospital (Mercy Hospital, Folsom, Calif.) was made. Since the patient could swallow, oral amoxicillin 2 grams were given stat. Additionally, the submandibular region was coated with the B5/B6 cream, and TID based on a prior 18 month clinical usage to bring about rapid analgesia, rapid edemalhematoma resolution and resolution of minor infective events. In an alternative embodiment the topical agent comprises at least 15% Vitamin B6 by weight.

At 5 pm, on hospital round, it was found that intravenous antibiotics were still pending. However, clinical digital exam of the cellulitis region revealed a stunning decrease in the tissue "board-like" cellulitis with a slight improvement in opening the mouth, less pain. CAT scans confirmed the inflammatory process of the infected region. Realizing the impact of B51B6 molecular transported cream to produce a reversal in 5 hours. Aggressive intravenous antibiotics, cream usage and tongue blade exercises allowed the removal of the tooth in the operating room with subsequent discharge home 54 hours after admission and a return to work 6 days after admission. Normal hospitalization for submandibular cellulitis is 6-10 days including radical surgical procedures, airway management and ICU care. This rapid reversal of clinical cellulitis by this invention's cream reflects on the similar rapid reversal of postoperative edema with dental extractions.

Intravenous care either for anesthesia or intravenous antibiotics is many times fraught with vein phlebitis. Interestingly application of B6 in a transport medium will with 3 times daily applications result in pain relief and resolution of the phlebitis in 3 to 4 days rather than the usual 6 to 8 weeks period of untreated care even when using heat. This resolution of a vein injury is very unusual to occur in a short time as now experienced in 5 cases over one year.

Nerve injury secondarily to anesthetic metabolites of local anesthetics is known as paresthesia.(2, 3) Paresthesia or anesthesia persistence of the facial nerves after dental treatment is extremely uncomfortable for the patient if it involves the tongue or lower lip. Two cases of paresthesia involving the right mandibular branch of the sensory nerve Cranial V are presented. Again both were treated post extraction of the third molar by topical B6 in a transport medium. The patients were a 55-year-old female and a 33-year-old female treated at different times. As stated in U.S. Pat. No. 5,776,859, paresthesia is a drug-induced injury to the pain fiber ion channels by metabolites of the local anesthetics. It does respond to 3 times a day application of the B6 transport cream over a 7-week period of time. The first patient was a 55-year reliable historian being a nurse who experienced altered lip/chin sensation. Weekly to biweekly visits revealed a 30% decrease in prior weeks distribution of paresthesia. On week 3, the patient came in on her own because of marked increase of pain in the lower right dental arch with marked hypesthesia of lip and chin area. At that point it was realized she had run out of the B5/B6 cream resulting in again a 7-week return to normal sensation. These clinical cases demonstrate the repair of a sensory nerve from a chemical toxicity over 7 weeks instead of 9-12 months. Further the safety of B6 to a nerve is predicted action of B6 and now shown not to cause further injury to a human sensory nerve.

Another application of B6 transport cream to a marked injury of head and neck region is the "boxer glove" injury of hematoma and edema to the periorbital and intraorbital tissues of the human eye socket.(4) An 84-year-old male sustained this injury on falling and was seen 6 hours after his fall with marked left cheek bone (zygoma). Eyelids were closed to the point that the patient could not open them. Application of the B51B6 cream resulted in his ability to open his eyelids just 7 minutes after topical application to the swollen areas of his face. I could then access his eye globe function and sight. The patient had marked midline deviation of crossing to his right about 45 degrees, no entrapment and full range of motion. The rapid decrease in eyelid swelling was noted by his adult daughter and myself and was repeated the next morning but now the eye deviation was 15 degrees. Apparently the overnight application of the B5/B6 cream reduced the edema and hematoma between the left lateral rectus orbital muscle and the bony orbit cavity. The significance of this case was the transported B6 was benign to the eye globe and was capable to transporting though orbital edema and bone structures.

Now when due consideration is made of B6's ability to penetrated the human skull, stop bleeding, resolves hematoma, and is neuron friendly, a serious proposal is that molecularly transported B6 from topical skin areas over the intracranial injury to abort a CNS stroke.(I) Further usefulness of B6 transport has resulted in it known ability to interfere with barbiturate general anesthesia. The barbiturate is attenuated and indeed this property has been used in my oral surgery practice to reverse barbiturate general anesthesia in 5-12 minutes rather than 70-90 minutes. By topical application over the wisdom tooth area at the beginning of the case, then the barbiturate reversal that occurs quickly at the end of the general anesthetic enhances patient safety and allows quick discharge from the office.

Bleeding from B6 during oral surgery routinely stops at minute 3. Facial hematoma resolution has occurred in 24-48 hours postoperatively. Consequently, the use of B6 in a molecular transport medium may abort a CNS stroke, promote rapid healing from the stroke and perhaps be invaluable to rehabulate the stroke victim. This action of transported B6 was proposed to National Institute of Health. A minor stroke was indeed reversed in a 45-year-old male. This patient sustained a heart attack that resulted in an embolus to his left optic nerve known as ischemic optic neuropathy, a condition that has no known cure and results in blindness.(5) The patient was medically seen and documented to be blind in his left eye and the condition had been this way for 2 weeks when the patient sought out the B5/B6 transport cream. After three days of topical usage over and around the affected eye, the patient's eyesight began to return. During this time B5/B6 usage, the patient's affected eye would experience flashes of color light prior to return of vision, the vision returning in small increments. Whenever the patient took a shower after placing the cream periorbital, he would experience even more intense light flashes and quicker vision improvement. This later observation then led to the need to add water droplets if the B6 cream became dry or cakey. Today this use of water as an additive to the cream is rationalized by the fact that the cream biochemical rates have increased so much in the application site that addition of water allows continued biochemical transport of residual topical cream. Medical evaluation during this time revealed hematoma resolution in the eye globe. His sight continued to improve until the patient had functional left eyesight at 6 weeks. As he continued his usage of the topical B6 transport cream, his eyesight returned to better function than before the minor stroke to his optic nerve. This improvement in eyesight has now been documented in 3 patients by medical evaluation and may lead to treating of eyesight problems including macular degeneration using a molecularly transported vitamin like B51B6 combination now employed in the current patent applications made by this inventor.

The B51B6 cream has also treated common headaches in 5 adult patients. Application of the vitamin is over the skin area of the skull headache and most interestingly within 2-4 minutes the headache disappears and does not return after a single application. Minor concussion pain to the skull has also been successfully treated using the B5/86 cream topically over the area of the trauma blow. The value of treating headache pain with a transported B6 is based on the ability of B6 to stop small pain nerve fibers from transmitting an impulse to the brain.(2) Based on U.S. Pat. No. 5,776,859 in which cancer was stated to be caused by the aniline metabolites of injected local anesthetics used in dentistry, this inventor was successful to get Federal Food and Drug approval of a cancer free local anesthetic in dentistry based on a thiophene ring rather than an amino benzene ring. This approval in late 2000 has now resulted in the clear decline of lung cancer in the United States for the first time in 90 years. Now that aminobenzene drug structures have been tied into cancer causation, there exists the real need in the United States for a headache replacement of acetaminophen pain relievers. Thus the novel use of topical B6 transported cream may make a simple and safe way to manage common headaches without the need of complex pharmaceuticals.

Another case of importance is the ability of the molecularly transported B6 to bring about an activation of a poorly functioning sub dermal gland, e.g. thyroid. Almost one third of the US population suffers from low thyroid function (hypothyroidism). A 48-year-old female came in to have an involved surgical removal of a tooth and she sought out my practice because of the reputation for rapid wound healing technology routinely being used for all patients. At the time of surgery, I noted her skin to be extremely dry and crusty/flakily and after surgery J found that her skin condition had existed ever since she had been treated with a radioisotope for thyroid cancer, had gone hypothyroid, but no thyroid surgery had been performed, she was 10 years after treatment and currently was on thyroid supplements. On return from surgery 3 days later, she reported a total resolution of the skin problem on her hand that she had used to apply the B5/B6 cream to her cheek skin opposite the surgical site. What impressed her most was that the skin on her hand was normal and now totally free of pain secondarily to lack of dermal cracking. I then suggested, knowing that some thyroid might still be present, applying the cream 2-3 times daily over the thyroid gland itself in her neck since her skin condition was truly head to toe and I could not envision this lady taking a head to toe bath in B6 cream. The patient returned 1 week later with very dramatic results. Her head to toe skin condition disappeared, her exothalopic proptosis of her eyes had suddenly reversed and now her eyes where sitting back in their orbital sockets and for the first time in years she could close her eyelids even when sleeping, and finally her low blood pressure had now returned to normal levels of 120/80; all these clinical things happening for the first time in 10 years with the use of B5/B6 cream over the area of the thyroid. Further follow-up has medical documentation that her serum thyroid levels are approaching normal and she may discontinue her thyroid supplementation. This patient's quality of life is remarkably improved and when she visits the office, all we can do is laugh and enjoy the radical result of a simple application now of B5/B6 transdermal cream twice daily. Further findings now include an improvement in her eyesight as well as documented by her optometrist.

Continued usage of BS/B6 in either a cream of gel in dental application has resulted in better patient management for acute moderate to severe pain. Application of the gel adjacent to a tooth with deep dental decay causing pain can bring about total pain relief in 1-3 minutes equivalent to a local anesthetic injection in the area. This inventor has proposed that the B6 can penetrate into the tooth pulpal tissues to decrease the inflammation in seconds and could potentially result in reversal of tooth pulpal pathology and avert a need for an extraction or root canal therapy.

In each application of BS/B6 cream for post surgical management, the patients over the last 3 years have all presented with little or no gingivitis of generalized evidence of poor dental hygiene. This observation is totally atypically for an oral surgery practice and normally that patients will require a professional visit with a hygienist 6 to 8 weeks after surgery to undergo a dental tooth cleaning for plaque and tartar. Since the BS/B6 gel or cream has reduced postoperative gingivitis, which is a known biochemical function of B6, it is only logical that toothpaste formulations should include molecularly transported B6 as a component in the toothpaste. Thus gingivitis that can lead to moderate or severe periodontal disease could and should be treated daily through the use of B6 cream or gel transported in a vehicle of a dental dentifrice, better known as toothpaste. Also topical pain relieving gels of B5/B6 could also be an additive to a dentifrice or as a separate topical application gel to control local dental pain for adults or even young children.

Insect bites can be very bothersome while B6 is well known to decrease tissue edema, promote an antibacterial environment in host tissues, reduce pain and promote white blood cell chemotaxis into an injury site. The B5/B6 topical cream has been used in bee stings to end pain in 1 minute and reduce edema and swelling in 4-6 hours making the injury a non event. Similar case reports for spider bites including the brown recluse spider have also responded rapidly to complete resolution using B5/B6 cream in hours rather than weeks. Many insect bites evoke an autoimmune response that clinically looks like an allergic reaction. Two adult cases, one 83-year-old male and one 22-year-old female, developed delayed hypersensitivity reactions to penicillin that was very difficult to diagnosis because the topical facial usage of B5/B6 cream postoperative. In fact, the aggressive usage of B5/B6 cream to areas of angioneurotic edema witnessed an overnight resolution for both patients. Finally concurrent usage of single low dose of steroids for contact dermitis with the B5/B6 cream results in hourly resolution instead of days to resolve. It appears B6 will enhance intravenous usage of steroids to reduce tissue edema in a synergistic mode of action to cause rapid resolution of the clinical problem.

Burns, first through third degree, response very nicely to the B5/B6 cream. Three well-documented cases of third degree burns in three patients all responded in 3-4 minutes to the application directly over the burn site with good pain relief that does not return after a single application. Continued application over the blister site does not produce molecular transport, but application around the blister site does. After three days, the blister can be drained and then the B6 will have access to the new healing skin ulcer to usually result in total healing in 10 days. Obviously, first and second-degree burns will respond in a very fast healing progress since there is not a dead skin barrier to transport like the third degree burn.

The B5/B6 cream discussed consists of calcium pantothenate powder 11 gram (5%), pyridoxine HCL powder 66 gram (30% and variable), ascorbic acid 2.42 gram, citric acid USP fine powder 2.42 gram, sodium metabisulfite FCC granulae 0.22 gram, lecithin/isopropyl palmitate solution 44 ml & pluronic F-127 20% aqueous solution 220 ml to make a mixture to be used topically on skin and oral mucosa. The B5/B6 gel consists of calcium pantothenate powder 10 gram, pyridoxine HCL powder 36 gram, ascorbic acid USP 1.1 gram, hydroxypropylcellulose 1500 powder 2.7 gram, citric acid USP monohydrate powder 1.1 gram, sodium metabisulfite FCC granulae 0.26667 gram, and finally dimethyl sulfoxide (DMSO) odorless liquid 100 ml again for topical use intraoral or on skin. For injection, B6 as component of the meperidine molecule can be used as an infiltrating agent in the injury site to bring about the events discussed in this invention.

Definitions

A. Molecular transport of B6 is a transmolecular event as out lined in FIG. 1 of U.S. patent application Ser. No. 10/318,940. B. A topical agent consists of components that allow molecular transport of B5/B6 or analogues and can take the form of cream, gel, jelly paste, glue, wax, ointment, semi-solid matter and gelatin. C. Increasing metabolic rate is a known function of coenzyme action of B6 and is further detailed in U.S. patent application Ser. No. 10/318,940. D. The molecular transport medium for said transmolecular Vitamin B6 may be but is not limited to DMSO or soy lecithin.

Therefore, the foregoing is considered as illustrative only of the principles of the invention. Further, since numerous modifications and changes will readily occur to those skilled in the art, it is not desired to limit the invention to the exact disclosure shown and described, and accordingly, all suitable modifications and equivalents may be resorted to, falling within the scope of the invention.

I claim:
1. A method of treating a patient using Vitamin B6 and Vitamin B5 in a molecular transport medium, comprising:
   a. applying adjacent to a tooth of said patient a topical agent comprising at least 15% by weight Vitamin B6 and at least 2.5% by weight Vitamin B5 in a molecular transport medium;
   b. wherein said molecular transport medium is selected from the group consisting of DMSO and soy lecithin;
   c. wherein said patient suffers dental pain; and d. wherein said Vitamin B6 and Vitamin B5 improve the condition of said dental pain through molecular transport.

2. The method of claim 1 wherein said molecular transport medium is DMSO.

3. The method of claim 1 wherein said molecular transport medium is soy lecithin.

4. A method of treating a patient, comprising:
   a. providing a patient with dental pain associated with a tooth, wherein the cells associated with said tooth have a metabolic rate;
   b. applying adjacent to said tooth of said patient a topical agent comprising transmolecular Vitamin B5/B6 in a molecular transport medium wherein said Vitamin B5/B6 alters said metabolic rate;
   c. wherein said molecular transport medium is selected from the group consisting of DMSO and soy lecithin; and
   d. wherein said topical agent comprises at least 15% by weight Vitamin B6 and at least 2.5% by weight of Vitamin B5.

5. The method of claim 4 wherein said molecular transport medium is soy lecithin.

6. The method of claim 4 wherein said molecular transport medium is DMSO.

7. A method of treating a patient, comprising:
   a. applying a topical transmolecular agent adjacent to a tooth of said patient, said topical transmolecular agent comprising at least 20% by weight Vitamin B6 and at least 2.5% by weight Vitamin B5 and a molecular transport medium;
   b. wherein said molecular transport medium is selected from the group consisting of DMSO and soy lecithin;
   c. wherein said patient suffers from dental pain; and
   d. wherein said topical transmolecular agent improves said dental pain through an alteration in metabolism.

8. The method of claim 7 wherein said molecular transport medium is DMSO.

9. The method of claim 7 wherein said molecular transport medium is soy lecithin.

\* \* \* \* \*